United States Patent
Cui et al.

(10) Patent No.: US 11,365,260 B2
(45) Date of Patent: Jun. 21, 2022

(54) AGONISTIC 4-1BB MONOCLONAL ANTIBODY

(71) Applicant: REYOUNG (SUZHOU) BIOLOGY SCIENCE & TECHNOLOGY CO., LTD, Suzhou (CN)

(72) Inventors: Wenjun Cui, Suzhou (CN); Shuhua Guo, Suzhou (CN)

(73) Assignee: REYOUNG (SUZHOU) BIOLOGY SCIENCE & TECHNOLOGY CO., LTD, Suzhou (CN)

( * ) Notice: Subject to any disclaimer, the term of this patent is extended or adjusted under 35 U.S.C. 154(b) by 220 days.

(21) Appl. No.: 16/755,136

(22) PCT Filed: Nov. 21, 2018

(86) PCT No.: PCT/CN2018/116705
§ 371 (c)(1),
(2) Date: Apr. 9, 2020

(87) PCT Pub. No.: WO2019/072274
PCT Pub. Date: Apr. 18, 2019

(65) Prior Publication Data
US 2020/0325236 A1 Oct. 15, 2020

(30) Foreign Application Priority Data

Oct. 12, 2017 (CN) .......................... 201710946874.X
Oct. 10, 2018 (CN) .......................... 201811177604.8

(51) Int. Cl.
| | | |
|---|---|---|
| C07K 16/28 | (2006.01) | |
| C07K 16/30 | (2006.01) | |
| A61K 39/395 | (2006.01) | |
| C12N 15/13 | (2006.01) | |
| C12N 5/10 | (2006.01) | |

(52) U.S. Cl.
CPC .......... *C07K 16/2878* (2013.01); *C07K 16/30* (2013.01); *C07K 2317/24* (2013.01); *C07K 2317/565* (2013.01)

(58) Field of Classification Search
CPC .......................... C07K 16/2878; C07K 16/30; C07K 2317/24; C07K 2317/56; C07K 2317/565; A61P 35/00; A61P 37/02; A61K 2039/505
See application file for complete search history.

(56) References Cited

FOREIGN PATENT DOCUMENTS

| | | |
|---|---|---|
| CN | 1440812 A | 9/2003 |
| CN | 1867585 A | 11/2006 |
| CN | 106413751 A | 2/2017 |

OTHER PUBLICATIONS

Dai, Jihong, Non-official translation: Interventional Therapy and Mechanism of Excited Anti-4-1 BB Monoclonal Antibody on Mouse Leaf Acid Nephropathy, Medicine & Public Health, Chinese Selected Doctoral Dissertations and Master's Theses Full-Text Databases, No. 1, Mar. 5, 2005, Abstract.

Sun, Y. L. et al. "Administration of Agonistic Anti-4-1BB Monoclonal Antibody Leads to the Amelioration of Experimental Autoimmune Encephalomyelitis" The Journal of Immunology, vol. 168, Dec. 31, 2002 (Dec. 31, 2002), pp. 1457-1465.

Tian, Xiaojing et al. Preparation of anti-human 4-1BB monoclonal antibody and analysis of its biological functions, Current Immunology, vol. 27. No. 3.Dec. 31, 2007 (Dec. 31, 2007), pp. 202-206.

Zhou, Huan et al. Preparation Of Anti-Human 4-1BB Monoclonal Antibody And Characterization Of Its Biological Activities, Chinese Journal of Cellular and Molecular Immunology, vol. 27, No. 9, Dec. 31, 2011, pp. 993-996.

*Primary Examiner* — Hong Sang
(74) *Attorney, Agent, or Firm* — Innovation Capital Law Group, LLP; Vic Lin

(57) ABSTRACT

An agonistic 4-1BB monoclonal antibody or an antigen binding fragment thereof, comprising a heavy chain variable region and a light chain variable region, the heavy chain variable region comprising: a CDR1 region having an amino acid sequence as shown in SEQ ID NO: 1, a CDR2 region having an amino acid sequence as shown in SEQ ID NO: 2, and a CDR3 region having an amino acid sequence as shown in SEQ ID NO: 3, the light chain variable region comprising: a CDR1 region having an amino acid sequence as shown in SEQ ID NO: 4, a CDR2 region having an amino acid sequence as shown in SEQ ID NO: 5, and a CDR3 region having an amino acid sequence as shown in SEQ ID NO: 6. The monoclonal antibody is targeted towards h4-1BB, and specifically binds to h4-1BB to activate T cells for treatment of a variety of cancers.

14 Claims, 3 Drawing Sheets
Specification includes a Sequence Listing.

SEQUENCE LISTING

<160> NUMBER OF SEQ ID NOS: 15

<210> SEQ ID NO 1
<211> LENGTH: 10
<212> TYPE: PRT
<213> ORGANISM: Artificial Sequence
<220> FEATURE:
<223> OTHER INFORMATION: Synthesized

<400> SEQUENCE: 1

Gly Tyr Ala Phe Thr Asn Tyr Trp Leu Gly
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthesized

<400> SEQUENCE: 2

Asp Ile Tyr Pro Gly Asn Gly Asn Ser Tyr Tyr Asn Glu Lys Phe Lys
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: Synthesized

<400> SEQUENCE: 3

Ser Ser Ser Tyr Tyr Arg Asp Val Met Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthesized

<400> SEQUENCE: 4

Arg Ala Ser Glu Asn Ile Tyr Ser Tyr Leu Val
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthesized

<400> SEQUENCE: 5

Asn Ala Lys Thr Leu Ala Glu
1               5

<210> SEQ ID NO 6
<211> LENGTH: 9
<212> TYPE: PRT
<213> ORGANISM: Artificial Sequence
<220> FEATURE:
<223> OTHER INFORMATION: Synthesized

<400> SEQUENCE: 6

Gln His His Tyr Gly Thr Pro Leu Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Synthesized

<400> SEQUENCE: 7

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Ala Phe Thr Asn Tyr
                20                  25                  30

Trp Leu Gly Trp Val Lys Gln Arg Pro Gly His Gly Leu Glu Trp Ile
            35                  40                  45

Gly Asp Ile Tyr Pro Gly Asn Gly Asn Ser Tyr Tyr Asn Glu Lys Phe
        50                  55                  60

Lys Gly Arg Ala Thr Leu Thr Ala Asp Lys Ser Ser Thr Val Tyr
65                  70                  75                  80

Met Gln Leu Ser Ser Leu Thr Ser Glu Asp Ser Val Val Tyr Phe Cys
                85                  90                  95

Thr Arg Ser Ser Ser Tyr Tyr Arg Asp Val Met Asp Tyr Trp Gly Gln
            100                 105                 110

Gly Thr Ser Val Thr Val Ser Ser
        115                 120

<210> SEQ ID NO 8
<211> LENGTH: 108
<212> TYPE: PRT
<213> ORGANISM: Artificial Sequence
<220> FEATURE:
<223> OTHER INFORMATION: Synthesized

<400> SEQUENCE: 8

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
                20                  25                  30

Leu Val Trp Tyr Gln Gln Lys Gln Gly Lys Ser Pro Gln Leu Leu Val
            35                  40                  45

Tyr Asn Ala Lys Thr Leu Ala Glu Gly Val Ser Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Leu
                85                  90                  95

Thr Phe Gly Ala Gly Thr Lys Leu Glu Leu Lys Arg
            100                 105

<210> SEQ ID NO 9
<211> LENGTH: 108
<212> TYPE: PRT
<213> ORGANISM: Artificial Sequence
<220> FEATURE:
<223> OTHER INFORMATION: Synthesized

<400> SEQUENCE: 9

Asp Ile Gln Leu Thr Gln Ser Pro Ser Phe Leu Ser Ala Ser Val Gly

```
              1               5                  10                 15
Asp Arg Val Thr Ile Thr Cys Arg Ala Ser Glu Asn Ile Tyr Ser Tyr
            20                 25                 30

Leu Val Trp Tyr Gln Gln Lys Pro Gly Lys Ala Pro Lys Leu Leu Ile
            35                 40                 45

Tyr Asn Ala Lys Thr Leu Ala Glu Gly Val Pro Ser Arg Phe Ser Gly
        50                 55                 60

Ser Gly Ser Gly Thr Glu Phe Thr Leu Thr Ile Ser Ser Leu Gln Pro
65                 70                 75                 80

Glu Asp Phe Ala Thr Tyr Tyr Cys Gln His His Tyr Gly Thr Pro Leu
                85                 90                 95

Thr Phe Gly Ala Gly Thr Lys Leu Glu Ile Lys Arg
              100                105
```

```
<210> SEQ ID NO 10
<211> LENGTH: 120
<212> TYPE: PRT
<213> ORGANISM: Artificial Sequence
<220> FEATURE:
<223> OTHER INFORMATION: Synthesized

<400> SEQUENCE: 10

Gln Val Gln Leu Val Gln Ser Gly Ala Glu Val Lys Lys Pro Gly Ala
1               5                  10                 15

Ser Val Lys Val Ser Cys Lys Ala Ser Gly Tyr Ala Phe Thr Asn Tyr
            20                 25                 30

Trp Leu Gly Trp Val Arg Gln Ala Pro Gly His Gly Leu Glu Trp Met
            35                 40                 45

Gly Asp Ile Tyr Pro Gly Asn Gly Asn Ser Tyr Tyr Ala Gln Lys Phe
        50                 55                 60

Gln Gly Arg Val Thr Met Thr Arg Asp Lys Ser Ser Ser Thr Val Tyr
65                 70                 75                 80

Met Glu Leu Ser Ser Leu Arg Ser Glu Asp Thr Ala Val Tyr Phe Cys
                85                 90                 95

Thr Arg Ser Ser Ser Tyr Tyr Arg Asp Val Met Asp Tyr Trp Gly Gln
              100                105                110

Gly Thr Leu Val Thr Val Ser Ser
        115                120
```

```
<210> SEQ ID NO 11
<211> LENGTH: 360
<212> TYPE: DNA
<213> ORGANISM: Artificial Sequence
<220> FEATURE:
<223> OTHER INFORMATION: Synthesized

<400> SEQUENCE: 11
caggttcagc tgcagcagtc tggagctgag ctggtaaggc ctgggacttc agtgaagata     60
tcctgcaagg cttctggata cgccttcact aactactggc taggttgggt aaagcagagg    120
cctggacatg gacttgagtg gattggagat atttaccctg gaaatggaaa ttcttactat    180
aatgagaagt tcaagggaag agccacactg actgcagaca atcctcgag cacagtctat     240 atgcagctca gtagcctgac atctgaggac tctgttgtct atttctgtac aagatcatcc    300
tcatactata gggatgttat ggactactgg ggtcaaggaa cctcagtcac cgtctcctcg    360

<210> SEQ ID NO 12
<211> LENGTH: 324
```

<212> TYPE: DNA
<213> ORGANISM: Artificial Sequence
<220> FEATURE:
<223> OTHER INFORMATION: Synthesized

<400> SEQUENCE: 12

```
gacatccaga tgactcagtc tccagcctcc ctatctgcat ctgtgggaga aactgtcacc    60
atcacatgtc gagcaagtga aaatatttac agttatttag tatggtatca gcagaaacag   120
ggaaaatctc ctcaactcct ggtctataat gcaaaaacct tagcagaagg tgtgtcatca   180
aggttcagtg cagtggatc aggcacacag tttctctga agatcaacag cctgcagcct    240
gaagattttg ggagttatta ctgtcaacat cattatggaa ctccgctcac gttcggtgct   300
gggaccaagc tggagctgaa acgg                                         324
```

<210> SEQ ID NO 13
<211> LENGTH: 450
<212> TYPE: PRT
<213> ORGANISM: Artificial Sequence
<220> FEATURE:
<223> OTHER INFORMATION: Synthesized

<400> SEQUENCE: 13

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Trp Leu Gly Trp Val Arg Gln Ala Pro Gly His Gly Leu Glu Trp Met
        35                  40                  45

Gly Asp Ile Tyr Pro Gly Asn Gly Asn Ser Tyr Tyr Ala Gln Lys Phe
    50                  55                  60

Gln Gly Arg Val Thr Met Thr Arg Asp Lys Ser Ser Thr Val Tyr
65                  70                  75                  80

Met Glu Leu Ser Ser Leu Arg Ser Glu Asp Thr Ala Val Tyr Phe Cys
                85                  90                  95

Thr Arg Ser Ser Ser Tyr Tyr Arg Asp Val Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

-continued

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 14
<211> LENGTH: 447
<212> TYPE: PRT
<213> ORGANISM: Artificial Sequence
<220> FEATURE:
<223> OTHER INFORMATION: Synthesized

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Trp Leu Gly Trp Val Arg Gln Ala Pro Gly His Gly Leu Glu Trp Met
        35                  40                  45

Gly Asp Ile Tyr Pro Gly Asn Gly Asn Ser Tyr Ala Gln Lys Phe
    50                  55                  60

Gln Gly Arg Val Thr Met Thr Arg Asp Lys Ser Ser Ser Thr Val Tyr
65                  70                  75                  80

Met Glu Leu Ser Ser Leu Arg Ser Glu Asp Thr Ala Val Tyr Phe Cys
                85                  90                  95

Thr Arg Ser Ser Ser Tyr Tyr Arg Asp Val Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 15
<211> LENGTH: 214
<212> TYPE: PRT
<213> ORGANISM: Artificial Sequence
<220> FEATURE:
<223> OTHER INFORMATION: Synthesized

<400> SEQUENCE: 15

Asp Ile Gln Leu Thr Gln Ser Pro Ser Phe Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Val Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His His Tyr Gly Thr Pro Leu
                85                  90                  95

```
Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135             140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

AGONISTIC 4-1BB MONOCLONAL ANTIBODY

TECHNICAL FIELD

The invention relates to antibodies, in particular to a monoclonal antibody that specifically binds to human 4-1BB.

STATEMENT REGARDING SEQUENCE LISTING

The sequence listing associated with this application is provided in text format in lieu of a paper copy and is hereby incorporated by reference into the specification. The name of the text file containing the sequence listing is NBSH-2020005p-seql.txt. The text file is 15.9 KB; was created on Apr. 9, 2020; and is being submitted via EFS-Web with the filing of the specification.

DESCRIPTION OF RELATED ART

Activation of T lymphocytes requires simulation of dual signals. The first signal is an antigen recognition signal provided by specific binding of antigen recognition receptors (TCR) on surfaces of T cells and MHC molecule-antigen peptide, and the second signal is a costimulatory signal (Chambers C A, et al. 1999. Curr Opin Cell Biol, 11(2):203-210) provided by binding of costimulatory molecules on surfaces of antigen presenting cells (APC) and corresponding receptors on the surfaces of the T cells. Only with combined action of the dual signals can the T cells be activated efficiently and proliferate to further play corresponding biological functions. In the absence of the costimulatory signal, the T cells are incapable or non-responsive (Seo S K, et al. 2003. J Immunol, 171(2): 576-583).

CD28 is the first costimulatory molecule discovered. The CD28/B7 synergistic stimulation signal plays a major role in the early stage of activation of the T cells, promotes its proliferation and maintains short-term survival (Boulougouris G, et al. 1998. J Immunol, 161(8): 3919-3924); 4-1BB/4-1BBL is a key costimulatory signal independent of the CD28/B7. Different from the CD28/B7 which plays the major role in the early stage of the activation of the T cells, the synergistic stimulation signal produced by the 4-1BB/4-1BBL acts mainly in the late response, can cooperate with the CD28 to further activate the T cells, especially is essential for maintaining the survival and effect functions of CD8+ T cells.

4-1BB (CD137; TNFRSF9) is a member of the tumor necrosis factor receptor superfamily and is a type I transmembrane glycoprotein expressed as a monomer or dimer on the surface of an activated T cell, mainly a CD8+ T cell and also expressed in a CD4+ T cell, a NK cell, a CD4+ CD25+ regulatory T cell, and the like.

Early studies have shown that the 4-1BB molecule is an activated costimulatory molecule that not only provides costimulatory signals to activate the T cells, thereby activating and proliferate the T cells, secreting cytokines and enhancing cytotoxic activity thereof, but also mediates reverse costimulatory signal, induces activation and proliferation of the APC and secretion of cytokines (Vinay D S, et al. 2006. J Mol Med (Berl), 84(9): 726-736), In vitro experiments have shown that a 4-1BB signal can play an immunomodulatory role in enhancing cell anti-infection and inhibiting tumor growth by promoting proliferation of the CD8+T cells and the CD4+T cells and secretion of cytokines. In animal tumor models, the use of the 4-1BB monoclonal antibody or the 4-1BBL gene into tumor cells can effectively induce cell-mediated anti-tumor immune response and promote tumor regression. In the study of the number and function of CD8+T after infection with 4-1BB/4-1BBL-deficient mouse virus, it is found that 4-1BB/4-1BBL interaction can enhance the killing function of virus-specific CD8 T cells and further can promote the survival and proliferation of memory T cells and control viral infection (Fuse S, et al. 2007. J Immunol, 178(8): 5227-5236). Subsequent studies have found that 4-1BB molecules have costimulatory activity and inhibitory effects in immune regulation. When the agonistic 4-1BB antibody is applied to an autoimmune disease model, the expression of IFN-γ, IDO and TGF-beta is up-regulated, and CD11+CD8+ regulates the proliferation of T cells in a large number, thereby inhibiting the proliferation and function of CD4+T cells, inhibiting the development of autoimmune diseases (Kim Y H, et al. 2009. J Leukoc Biol, 85(5):817-825). Activation of the 4-1BB pathway not only promotes the infiltration of the T cells into a transplanted organ, shortens the survival time of the transplanted organ and exacerbates the host's resistance to graft rejection, but also promotes CD4+ and CD8+ T cell-mediated graft-versus-host responses. Thus, to block the 4-1BB pathway between donor T cells and the receptor can reduces the host's resistance to graft rejection.

Therefore, it is possible to regulate the immune function of lymphocytes by interfering with the action of the 4-1BB signaling pathway, that is, by activating or blocking the 4-1BB/4-1BBL signaling pathway by antibodies against human 4-1BB, so that purposes of treatment or prevention of diseases such as cancers, autoimmune diseases, viral infections or graft-versus-host reactions can be achieved.

BRIEF SUMMARY OF THE INVENTION

The technical problem to be solved by the invention is to provide an antibody which specifically binds to human 4-1BB and does not block the binding of h4-1BBL to h4-1BB. The agonistic 4-1BB monoclonal antibody can also activate the 4-1BB/4-1BBL signaling pathway, enhance the T cell-mediated immune response, is anti-tumor, anti-infective and plays a regulation role in autoimmune diseases.

In order to solve the above technical problems, the invention adopts the following technical solutions:

The object of the invention is to provide an agonistic 4-1BB monoclonal antibody or antigen-binding fragment thereof; the agonistic 4-1BB monoclonal antibody or antigen-binding fragment thereof comprises a heavy chain variable region and a light chain variable region; the heavy chain variable region comprises the heavy chain variable region comprises a CDR1 region having an amino acid sequence as shown in SEQ ID NO: 1, a CDR2 region having an amino acid sequence as shown in SEQ ID NO: 2, and a CDR3 region having an amino acid sequence as shown in SEQ ID NO: 3; and the light chain variable region comprises a CDR1 region having an amino acid sequence as shown in SEQ ID NO: 4, a CDR2 region having an amino acid sequence as shown in SEQ ID NO: 5, and a CDR3 region having an amino acid sequence as shown in SEQ ID NO: 6.

According to one embodiment, the agonistic 4-1BB monoclonal antibody or the antigen binding fragment thereof comprises the heavy chain variable region as shown in SEQ ID NO: 7.

According to another embodiment, the agonistic 4-1BB monoclonal antibody or the antigen binding fragment thereof comprises the light chain variable region as shown in SEQ ID NO: 8.

According to preferred embodiment, the agonistic 4-1BB monoclonal antibody or the antigen binding fragment comprises the heavy chain variable region as shown in SEQ ID NO: 7 and the light chain variable region as shown in SEQ ID NO: 8.

According to some embodiments, the agonistic 4-1BB monoclonal antibody has one or more of the following properties:
(a) specifically binding to the human 4-1BB,
(b) activating the T cells,
(c) inhibiting tumor cell growth and
(d) treating cancers.

According to one specific embodiment, the agonistic 4-1BB monoclonal antibody comprises a heavy chain and a light chain.

In the invention, the agonistic 4-1BB monoclonal antibody is IgG, IgA, IgE, IgM or IgD, preferably IgG.

Furthermore, the agonistic 4-1BB monoclonal antibody is IgG1, IgG2, IgG3 or IgG4, preferably subclass IgG1.

Another object of the invention is to provide a humanized anti-human 4-1BB which is formed by humanized transformation of the agonistic 4-1BB monoclonal antibody.

According to a preferred embodiment, the humanized anti-human 4-1BB antibody comprises a light chain and a heavy chain; the sequence of the light chain is as shown in SEQ ID NO:9; and the sequence of the heavy chain is as shown in SEQ ID NO:10.

The third object of the invention is to provide a preparation method of the humanized anti-human 4-1BB antibody, in which, the agonistic 4-1BB monoclonal antibody is subjected to humanized transformation by adopting a way of template replacement.

The fourth object of the invention is to provide a derivative of the agonistic 4-1BB monoclonal antibody; the derivative of the agonistic 4-1BB monoclonal antibody is an antibody obtained after the amino acid sequence of the agonistic 4-1BB monoclonal antibody is modified or an antibody obtained after the amino acid sequence of the humanized anti-human 4-1BB antibody is modified.

The fifth object of the invention is to provide a nucleic acid encoding the agonistic 4-1BB monoclonal antibody, the antigen-binding fragment thereof or the humanized anti-human 4-1BB antibody.

The sixth object of the invention is to provide a host cell expressing the nucleic acid.

The seventh object of the invention is to provide a preparation method of the agonistic 4-1BB monoclonal antibody, the preparation method comprising the steps of
(a) immunizing mice by using antigens to prepare hybridoma cells;
(b) screening positive hybridoma cells;
(c) cloning the nucleic acid sequence of the light and heavy chain variable regions of the antibody, and ligating with the constant region of human IgG1 to construct a eukaryotic expression vector; and
(d) transfecting a host cell expression antibody, and purifying the antibody to obtain a monoclonal antibody against 4-1BB.

The eighth object of the invention is to provide application of the agonistic 4-1BB monoclonal antibody or antigen-binding fragment thereof in preparation of drugs for inhibiting tumor cell growth, inflammation and development of autoreactive diseases.

The ninth object of the invention is to provide a pharmaceutical composition, comprising the agonistic 4-1BB monoclonal antibody or the antigen-binding fragment thereof and a pharmaceutically acceptable vector.

Due to implementation of the above technical solutions, the invention, compared with the prior art, has the following advantages:

The invention provides a monoclonal antibody against h4-1BB or a humanized anti-human 4-1BB antibody which specifically binds to h4-1BB to further activate the T cells. The antibody of the invention has application potentials in treating of a variety of cancers by means of immunomodulatory effects.

DETAILED DESCRIPTION OF THE INVENTION

Figure 1:
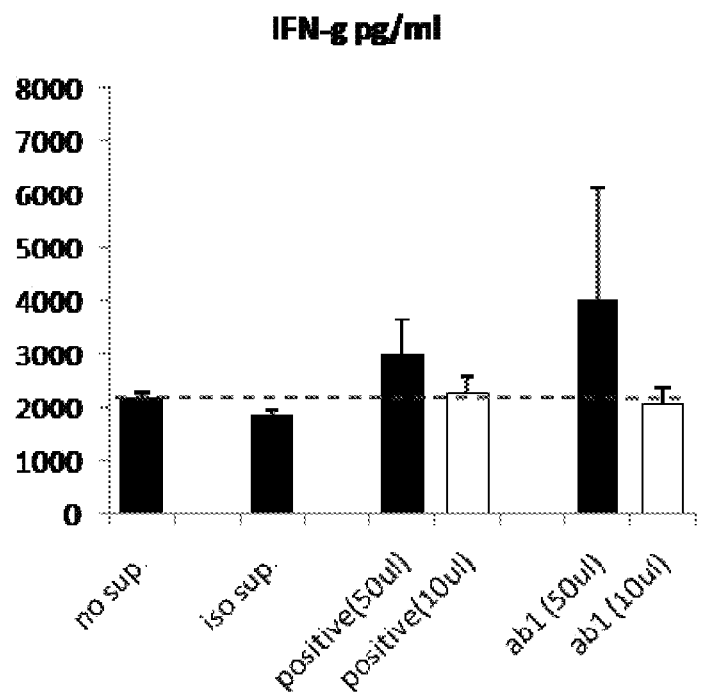
FIG. 1 is a graph showing the results of in vitro activation of human PBMC by an antibody ab1 secreted by a hybridoma.

The "antibody (Ab)", an immunoglobulin (Ig), is a glycoprotein that specifically binds to an antigen, and is produced by a plasma cell which is proliferated and differentiated by B cells after being stimulated by the antigen. The antibody is presented in the form of one or more Y-type monomers consisting of two heavy chains and two light chains, wherein each heavy chain comprises three highly variable regions, namely, H-CDR1, H-CDR2 and H-CDR3 and three constant regions (CH1, CH2 and CH3); and each light chain includes three highly variable regions, namely, L-CDR1, L-CDR2 and L-CDR3 and a constant region. The heavy chain is divided into mu, sigma, gamma, alpha and epsilon chains. According to different heavy chains, the antibody can be divided into five types, including, IgM, IgD, IgG, IgA and IgE, and the light chain has two types, that is, kappa and lambda. The variable regions of the light and heavy chains of the antibody are the antigen binding sites responsible for the recognition and binding of the antigen, and the constant region is associated with the biological effects of the antibody.

The "chimeric antibody" of the invention refers to a genetically engineered antibody in which a constant region of a human immunoglobulin is spliced with a variable region of a murine antibody.

The "monoclonal antibody" of the invention is an antibody that is highly homologous to a particular epitope. The monoclonal antibody, different from a polyclonal antibody with multiple antigenic determinants aiming at a certain antigen, is not easily cross-reactive with different antigens, and is highly specific.

The "antigen-binding fragment" of the invention refers to one or more parts of an antibody that retains activity of binding to an antigen.

The "anti-human 4-1BB antibody" of the invention refers to an antibody which specifically binds to human 4-1BB.

The "agonist" of the invention refers to an anti-human 4-1BB antibody involved in the invention. The anti-human 4-1BB antibody activates the 4-1BB/4-1BBL signaling pathway by binding to human 4-1BB so as to promote activation and proliferation of the T cells and secretion of cytokines and further to increase the expression of the costimulatory molecules on the surfaces of the T cells.

The "specific binding" of the invention refers to the ability of an antibody to interact with an antigen of a species under specific conditions rather than reacting with other antigens of the same family of antigens. The specific binding effect of the antibody can be determined by using methods such as ELISA, FACS and Western blot.

The "nucleic acid" as used in the invention refers to a genome, cDNA and a recombinant nucleic acid molecule which are separated from other components of the same source. A nucleic acid herein is a gene fragment encoding an interested target protein.

The "vector" as used in the invention refers to a DNA molecule capable of surviving on a host cell and autonomously replicating, containing a plurality of restriction enzyme sites and a marker gene and is a carrying tool capable of introducing a nucleic acid sequence encoding the target protein into a host cell and expressing the carried genetic information.

The "host cell" of the invention refers to a foreign gene expression system that expresses a target gene sequence. Host cells include prokaryotic cells and eukaryotic cells.

In some embodiments, the antibody comprises an H-CDR1 region having the amino acid sequence as shown in SEQ ID NO: 1, an H-CDR2 region having the amino acid sequence as shown in SEQ ID NO: 2 and an H-CDR3 region having the amino acid sequence as shown in SEQ ID NO: 3; in some other embodiments, the antibody comprises an L-CDR1 region having the amino acid sequence as shown in SEQ ID NO: 4, an L-CDR1 region having the amino acid sequence as shown in SEQ ID NO: 5 and an L-CDR3 region having the amino acid sequence as shown in SEQ ID NO: 6.

The antibody or antigen-binding fragment provided by the invention comprises a heavy chain variable region as shown in SEQ ID NO: 7 and a light chain variable region as shown in SEQ ID NO: 8.

```
Specifically, SEQ ID NO: 1: GYAFTNYWLG.

Specifically, SEQ ID NO: 2: DIYPGNGNSYYNEKFKG.

Specifically, SEQ ID NO: 3: SSSYYRDVMDY.

Specifically, SEQ ID NO: 4: RASENIYSYLV.

Specifically, SEQ ID NO: 5: NAKTLAE.

Specifically, SEQ ID NO: 6: QHHYGTPLT.

Specifically, SEQ ID NO: 7:
QVQLQQSGAELVRPGTSVKISCKASGYAFTNYWLGWVKQRPGHGLEWIGD

IYPGNGNSYYNEKFKGRATLTADKSSSTVYMQLSSLTSEDSVVYFCTRSS

SYYRDVMDYWGQGTSVTVSS.
```

```
Specifically, SEQ ID NO: 8:
DIQMTQSPASLSASVGETVTITCRASENIYSYLVWYQQKQGKSPQLLVYN

AKTLAEGVSSRFSGSGSGTQFSLKINSLQPEDFGSYYCQHHYGTPLTFGA

GTKLELKR.
```

In some embodiments, the antibody involved in the invention has at least one of the following properties:
(a) specifically binding to the human 4-1BB;
(b) activating the T cells;
(c) inhibiting tumor cell growth; and
(d) treating cancers.

The anti-human 4-1BB monoclonal antibody of the invention is IgG, IgA, IgE, IgM or IgD, preferably IgGm, wherein IgG is divided into four subclasses, including, IgG1, IgG2, IgG3 and IgG4, preferably, IgG1. The anti-human 4-1BB antibody can be subjected to the class switching by using the common methods in the field.

The antibody involved in the invention can be prepared by known methods in the field, including, a B cell hybridoma technique and a recombinant antibody technique and the like.

An antigen binding fragment of any anti-4-1BB antibody of the invention is provided in the invention.

The antigen binding fragment may comprise any sequence of the antibody, wherein amino acid sequences included in the antigen binding fragment are as follows:
(a) a heavy chain of the anti-4-1BB antibody;
(b) a light chain of the anti-4-1BB antibody;
(c) a heavy chain variable region of the anti-4-1BB antibody;
(d) a light chain variable region of the anti-4 BB antibody;
(e) one or more CDRs of the anti-4-1BB antibody; and
(f) three CDRs of the heavy chain and three CDRs of the light chain of the anti-4-1BB antibody.

In one aspect, the invention provides any derivative of the anti-human 4-1BB antibody.

In some aspects, the derivative of the anti-human 4-1BB antibody is derived from the modification of the amino acid sequence of the exemplary antibody ("original antibody") while the molecular structure of the amino acid sequence of the original antibody remains unchanged Amino acid insertions, deletions, substitutions or combinations of amino acid sequences of the framework regions, highly variable regions and constant regions of the original antibody may occur.

The antibody of the invention may undergo a process in which an amino acid is substituted with a similar amino acid. This process is called conservative substitution, and an antibody produced by the conservative substitution generally does not affect the binding activity of the antibody. The substitution types are as follows: alanine, leucine, isoleucine, valine, proline, phenylalanine, tryptophan, methionine, glycine, serine, threonine, cysteine, tyrosine, asparagine, glutamine, arginine, lysine, histidine, aspartic acid and glutamic acid.

The antibody of the invention can be prepared by using prokaryotic expression systems such as *Escherichia coli* or eukaryotic expression systems such as CHO cells. Among them, the mammalian expression system is an optimal choice for expressing the antibody of the invention. Host cells used for expression antibodies include: CHO cells, HEK 293 cells, yeast, COS (African green monkey fibroblast cell line) cell lines, NSO myeloma cells, and Sp2/0 cells.

The antibody of the invention can be used for regulating activity of the T cells and enhancing cell-mediated immune responses. The antibody of the invention is suitable for treating cancers, assisting other drugs in treating cancers, and inhibiting autoimmune diseases.

Embodiment 1: Preparation of Hybridoma

The variable regions of the heavy and light chains of the antibody of the invention are initially obtained from hybridoma cells. The hybridoma cells are prepared by repeatedly immunizing Balb/c mice 3 times with human 4-1BB-Fc fusion proteins and an equal amount of IFA and performing cell fusion on spleen cells of immunized mice having an appropriate antibody titer and myeloma cells of mice according to a conventional way.

Screening of Hybridoma Supernatant

ELISA screening of hybridoma cells that bind to human 4-1BB: in order to screen anti-h4-1BB positive hybridoma cells, diluting h4-1BB-Fc fusion proteins to 0.5 μg/mL in a PBS buffer solution, coating 100 μL/well with an ELISA plate and staying overnight at 4 DEG C.; then discarding the solution, washing three times with PBST, then blocking with 3% BSA-PBST at 37 DEG C. for 1 h; discarding the solution, washing three times with a PBST washing plate and then adding 100 μL hybridoma supernatant for incubation at 37 DEG C. for 1 h; and washing the ELISA plate according to the above-mentioned method, co-incubating with a peroxidase labeled goat-anti-mouse IgG-Fc γ antibody at 37 DEG C. for 1 h and then washing the plate, adding 100 μL TMB substrate for incubation at 37 DEG C. for 20 min, and finally terminating with 50 μL sulfuric acid and reading the plate at 450 nm of an ELIASA.

ELISA screening of hybridoma cells that do not bind to human IgG: for screening anti-h4-1BB positive hybridoma cells, diluting hIgG to 1 μg/mL in a PBS buffer solution, coating 100 μL/well with an ELISA plate and staying overnight at 4 DEG C.; then discarding the solution, washing three times with PBST, then blocking with 3% BSA-PBST at 37 DEG C. for 1 h; discarding the solution, washing three times with a PBST washing plate and then adding 100 μL hybridoma supernatant for incubation at 37 DEG C. for 1 h; and washing the ELISA plate according to the above-mentioned method, co-incubating with a peroxidase labeled goat-anti-mouse IgG-Fcγ antibody at 37 DEG C. for 1 h and then washing the plate, adding 100 μL TMB substrate for incubation at 37 DEG C. for 20 min, and finally terminating with 50 μL sulfuric acid and reading the plate at 450 nm of the ELIASA.

FACS screening of hybridoma cells that bind to human 4-1BB: for screening hybridoma cells that bind to h4-1BB, co-incubating CHO-K1 expressing h4-1BB and the hybridoma supernatant, then binding the CHO-K1 to ifluor 647 labeled goat-anti-mouse IgG secondary antibody, using a corresponding mother cell line as negative control, mouse IgG as isotype control and commercial anti-4-1BB mAb as positive control at the same time and analyzing by using FACS.

Activation characteristics of the antibody: in vitro experiments determine the T cell activation of antibody to human PBMC. The in vitro experiment comprises steps of firstly separating CD3+ T cells from the human PBMC, co-incubating CD3+ T cells which are activated by using anti-CD3 mAb with the hybridoma supernatant, determining secretion of IFN-γ by the ELISA method and showing the activation activity of the antibody to the T cells indirectly through determination of the secretion of the IFN-γ. The result, as shown in the FIG. 1, shows that the excreted antibody ab1 produced by the hybridoma can significantly stimulate the activity of the T cells and promote the T cells to secrete the IFN-γ.

The secreted antibody can be further expanded and sub-cloned, together with hybridoma cells that bind to h4-1BB. After the positive hybridoma cells are counted, each mother clone is covered with two 96-well plates by using a limiting dilution method until the positive rate of antibody secretion is greater than 95%, and the culture is expanded and cryopreservation in liquid nitrogen is carried out in time.

Embodiment 2: Preparation of Anti-h4-1BB Chimeric Antibody

Preparation of antibody cDNA: the total RNAs of the hybridoma cells prepared in the embodiment 1 are extracted by using a guanidinium isothiocyanate-phenol-chloroform method, and with the RNA as a template, the first chain of the cDNA is synthesized by using a cDNA synthetic kit.

Gene cloning and sequence analysis of variable regions of the antibody: performing PCR amplification on VH and VL sequences of the antibody by adopting a documented universal primer and regarding the first chain of the cDNA as a template; connecting the VH and VL respectively to a T vector and transforming *Escherichia coli*; and sequencing after positive bacteria are authenticated through colony PCR, and confirming genes of the light and heavy chains of the antibody in the sequencing result by using IMGT/QUEST and IgBlast analysis software.

Construction of the eukaryotic expression vector of the chimeric antibody: splicing the sequence of the V region of the heavy chain of the murine antibody and a human IgG1 CH gene into a pRBH5 vector, and splicing the sequence o the V region of the light chain and a human IgG C κ gene into a pRBL2 vector; then carrying out sequencing determination, wherein the sequencing determination result show that the eukaryotic expression vector of the chimeric antibody: comprises a nucleotide sequence of the variable region of the heavy chain as shown in SEQ ID NO: 11 and a nucleotide sequence of the variable region of the light chain as shown in SEQ ID NO: 12.

SEQ ID NO: 11 caggttcagctgcagcagtctggagctgagctggtaaggcctgggacttc agtgaagatatcctgcaaggcttctggatacgccttcactaactactggc taggttgggtaaagcagaggcctggacatggacttgagtggattggagat atttaccctggaaatggaaattcttactataatgagaagttcaagggaag agccacactgactgcagacaaatcctcgagcacagtctatatgcagctca gtagcctgacatctgaggactctgttgtctatttctgtacaagatcatcc tcatactatagggatgttatggactactggggtcaaggaacctcagtcac cgtctcctcg

SEQ ID NO: 12 gacatccagatgactcagtctccagcctccctatctgcatctgtgggaga aactgtcaccatcacatgtcgagcaagtgaaaatatttacagttatttag tatggtatcagcagaaacagggaaaatctcctcaactcctggtctataat gcaaaaaccttagcagaaggtgtgtcatcaaggttcagtggcagtggatc aggcacacagttttctctgaagatcaacagcctgcagcctgaagattttg -continued ggagttattactgtcaacatcattatggaactccgctcacgttcggtgct gggaccaagctggagctgaaacgg Expression and purification of the chimeric antibody: transfecting HEK 293F cells by recombinant plasmid extracted by the kit through a cationic polymer method and transfecting empty plasmid to serve as a control at the same time; collecting cultural supernatant of the HEK 293F cells which have been transfected the plasmid after 6 days; separating and purifying the chimeric antibody by using a Protein A affinity column; and dialysing the purified antibody with PBS.

Embodiment 3: Identification of In Vitro Activity of Antibodies

Affinity of the antibody: determining binding kinetics of the purified antibody which is prepared in the embodiment 2 and the h4-1BB by using BIAcore T200; coupling 1 mg/mL antigen (h4-1BB-Fc fusion protein) to the surface of a CMS chip by using an amino coupling method, binding at 30 μL/min for 300 s when the concentration of the antibody is within 0.3125-5.0 μg/mL and then dissociating for 300 s; and analyzing data recorded by the Biacore T200 by using Biacore T200 Evaluation Software, wherein analysis results are as shown in Table 1.

TABLE 1

| Antibody clone No. | $k_a$ (M$^{-1}$S$^{-1}$) | $k_d$ (S$^{-1}$) | $K_D$ (M) |
|---|---|---|---|
| Ab1 | $1.46 \times 10^5$ | $1.37 \times 10^{-5}$ | $9.34 \times 10^{-11}$ |

Activation characteristics of antibodies: the activation of human PBMC by the purified antibody prepared in the embodiment 2 is determined in vitro experiment. First, blood is collected by using an anticoagulated blood collection tube, and the mixture of blood and anticoagulant in the blood collection tube is added to a centrifuge tube; the blood collection tube is uniformly washed with the DPBS and centrifuged at 2000 rpm/min for 10 min; the upper layer plasma is discarded, and the lower blood cells are diluted with an equal volume of DPBS; then the diluted lower blood cells are slowly added to Ficoll to be centrifuged at 2000 rpm/min for 10 min for density gradient centrifugation; the supernatant is discarded, the PBMC is slowly aspirated and DPBS is added to wash the PBMCs; the washed PBMCs is centrifuged at 2000 rpm/min for 10 min and then the supernatant is discarded; the PBMC is resuspended by the DPBS and is centrifuged at 1200 rpm/min for 10 min; and a complete medium (RPMI1649+10 WT % FBS+1 wt % PS) is aspirated to resuspend the PBMCs until the cell density is 5*10<7> cells/mL.

Figure 2:
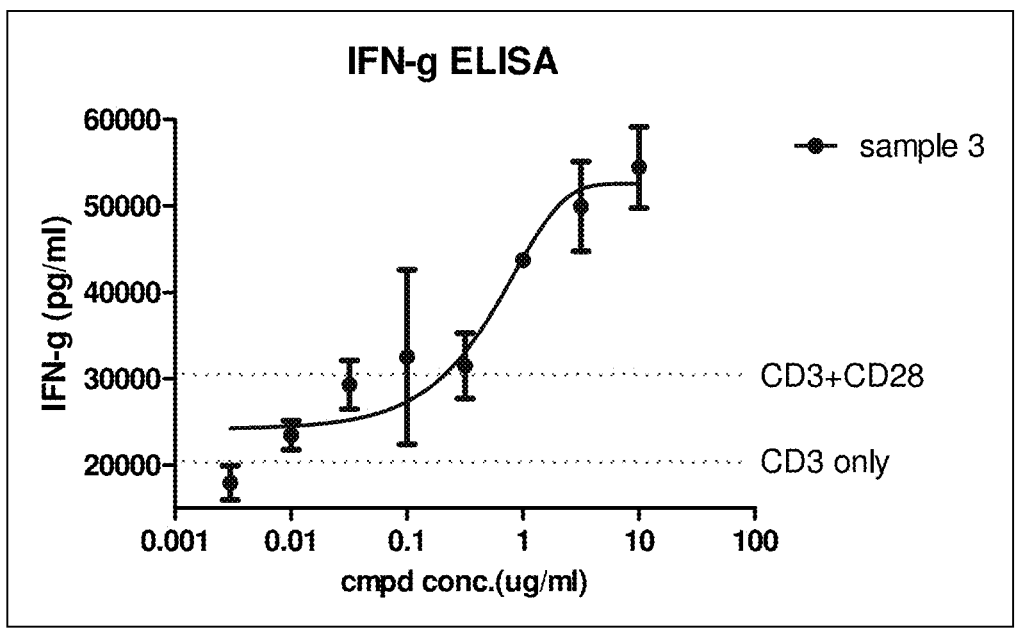
FIG. 2 is a graph showing the results of in vitro activation of human PBMC by an ab1 chimeric antibody.

PBMCs (2*10<5> cells/well) are activated by using anti-CD3 mAb (1 μg/mL), and then incubated with the anti-h4-1BB monoclonal antibody (10 μg/mL is diluted in a 3-fold gradient and 8 concentration gradients in total are provided). CD28 (2 μg/mL) is used as a positive control. Finally, secretion of the IFN-γ is determined by the ELISA method, and the activation activity of the antibody for the PBMCs is indirectly reflected by the determination of the secretion of the IFN-γ. The in vitro activation of the ab1 chimeric antibody for the T lymphocytes in human PBMCs is shown in FIG. 2. Wherein, the activation of the ab1 chimeric antibody for the ab1 chimeric antibody obviously depends on the concentration.

Embodiment 4: Binding Specificity of Antibodies

Figure 3:
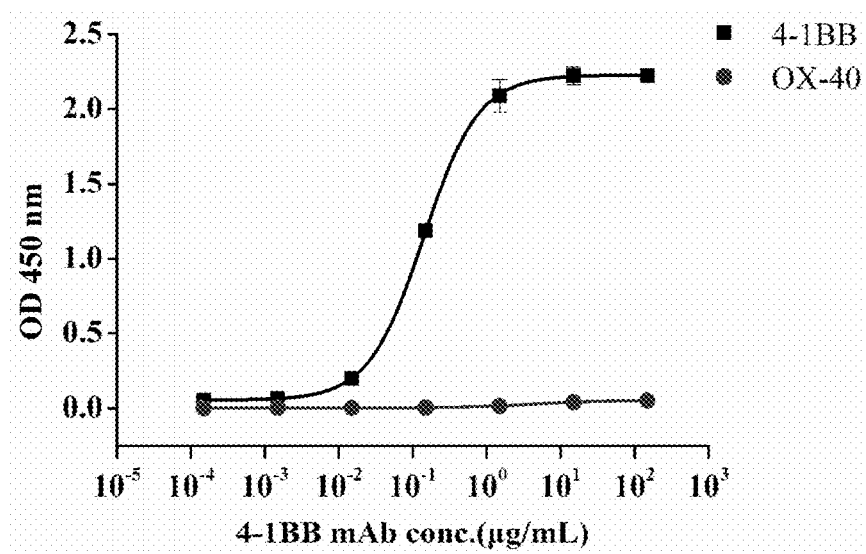
FIG. 3 is a graph showing the results of specific binding of the ab1 chimeric antibody and the human 4-1BB.

The binding specificity of the anti-human 4-1BB antibody ab1 is determined by ELISA. The ELISA comprises steps of coating human OX-40 or 4-1BB protein (1 μg/mL) with an ELISA plate, incubating overnight at 4 DEG C.; washing three times with PBST (0.1% Tween 20) and blocking with 3% BSA for 1 h; washing three times, adding the purified anti-human 4-1BB antibody ab1 prepared in the embodiment 2 and incubating for 1 h; washing three times and adding horse radish peroxidase (HRP) labeled goat-anti-human IgG (1:2000 dilution) and incubating for 1 h; washing three times, then adding a substrate solution (TMB) and developing the color at room temperature in the dark; finally, adding a stop solution (2N H$_2$SO$_4$) and reading the optical density (OD) value at 450 nm. The results show that the anti-human 4-1BB antibody with clone No. 58A10H5 can specifically bind to human 4-1BB without non-specific binding to its homologous member OX-40, as shown in FIG. 3.

Embodiment 5: Cross-Reactivity of Species of Antibodies

Figure 4:
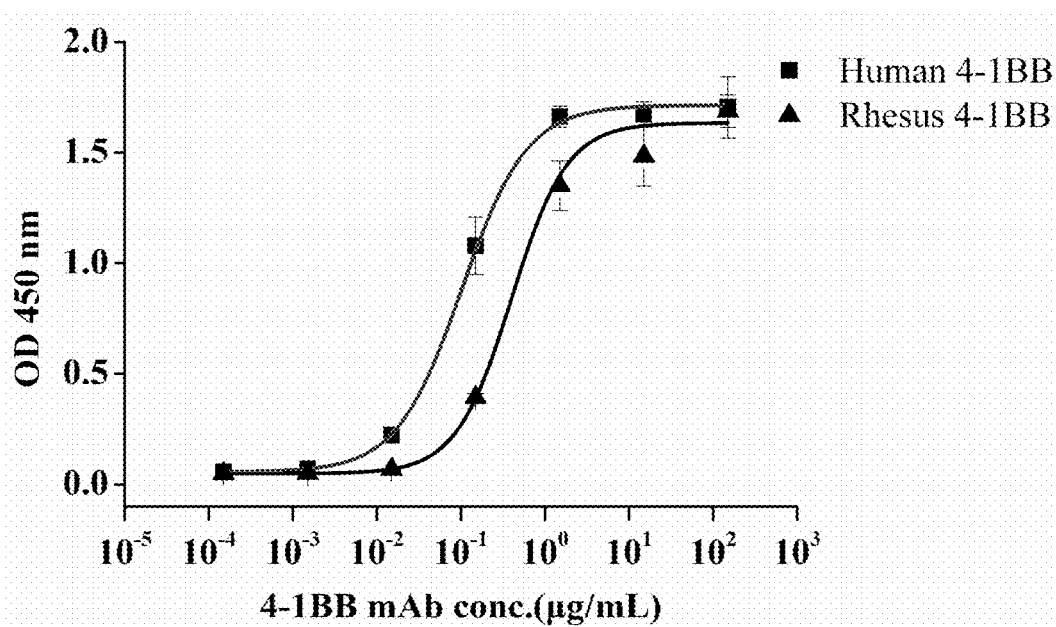
FIG. 4 is a graph showing the cross-reactivity of species of the ab1 chimeric antibody.

The cross-reactive activity of the antibody with cynomolgus monkey 4-1BB molecules is determined by ELISA. The ELISA comprises steps of coating the human 4-1BB or cynomolgus monkey 4-1BB (1 μg/mL) with the ELISA plate, incubating overnight at 4 DEG C.; washing three times with PBST (0.1% Tween 20), blocking with 3% BSA for 1 h; washing three times, adding the purified anti-human 4-1BB antibody prepared in the embodiment 2 and incubating for 1 h; washing three times and adding horse radish peroxidase (HRP) labeled goat-anti-human IgG (1:2000 dilution) and incubating for 1 h; washing three times, then adding the substrate solution (TMB) and developing the color at room temperature in the dark; and finally, adding the stop solution (2N H$_2$SO$_4$) and reading the optical density (OD) value at 450 nm. The results are shown in FIG. 4. From a fitting curve, the EC50 of the antibody and the human 4-1BB is 0.67 nM, the EC50 of the antibody and the cynomolgus monkey 4-1BB protein is 2.67 nM and the cross-reactive activity exits between the anti-human 4-1BB antibody and the cynomolgus monkey 4-1BB proteins in the experiment.

Embodiment 6: Humanized Anti-Human 4-1BB Antibodies

Figure 5:
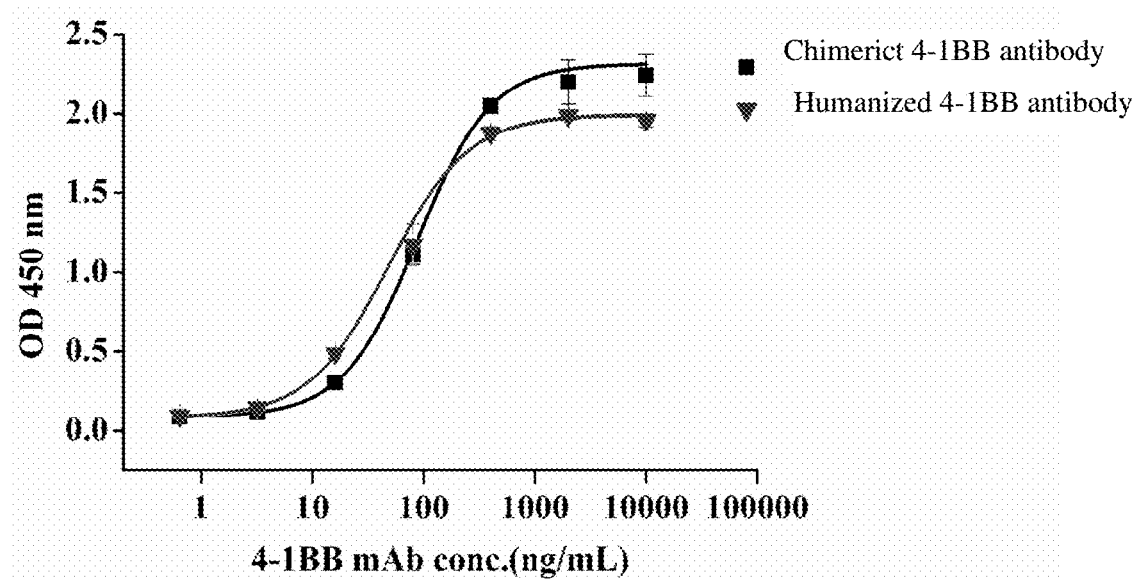
FIG. 5 is a graph showing changes in the binding activity of the ab1 antibody before and after humanization, detected by adopting ELISA.

To further reduce immunogenicity of the anti-human 4-1BB antibody ab1, humanized transformation is carried out by using template replacement in the invention. The humanized transformation comprises steps of firstly searching a humanized antibody which is homologous with the amino acid sequences of VH or VL of the antibody online by using Blastp; then generating a three-dimensional space model of the antibody by using easymodeller; then introducing the model into a SAVES server and judging the feasibility of the model; selecting an antibody germ-line gene with the highest homology as a humanized antibody template according to analysis on comparative information of the antibody sequence and the humanized sequence; dividing a framework region and a height variable region of the template and the target antibody by using an IMGT website; replacing the variable region of the template with the variable region of the target antibody; in combination with the modelling result and the sequence of the antibody variable region, obtaining sequence information of the key amino acid; then enabling the key amino acid in a murine variable region to undergo back mutation to obtain the humanized antibody sequence, wherein the sequence of the light chain is shown in SEQ ID NO: 9, and the sequence of the heavy chain is shown in SEQ ID NO: 10; and finally, synthesizing the humanized antibody gene and constructing the humanized antibody gene into the expression vector (pRBH5/pRBL2) of the lab, transfecting the HEK293 cells with the chimeric antibody and the humanized antibody, purifying by using Protein A and then detecting the changes of the binding activity of the antibody before and after the humanization by using the ELISA. The results are shown in FIG. 5.

```
                                                      SEQ ID NO: 9
DIQLTQSPSFLSASVGDRVTITCRASENIYSYLVWYQQKPGKAPKLLIYN

AKTLAEGVPSRFSGSGSGTEFTLTISSLQPEDFATYYCQHHYGTPLTFGA

GTKLEIKR

SEQ ID NO: 10
QVQLVQSGAEVKKPGASVKVSCKASGYAFTNYWLGWVRQAPGHGLEWMGD

IYPGNGNSYYAQKFQGRVTMTRDKSSSTVYMELSSLRSEDTAVYFCTRSS

SYYRDVMDYWGQGTLVTVSS
```

Embodiment 7: Antineoplastic Activity of Humanized Monoclonal Antibody of the Anti-Human 4-1BB Antibody Ab1

The humanized heavy chain variable region sequence of ab1 obtained in the embodiment 6 is spliced with the heavy chain constant region sequences of human IgG1 and IgG4 to obtain humanized ab1 IgG1 and IgG4 heavy chain complete sequences. The sequences are shown in SEQ ID NO; 13 and SEQ ID NO: 14.

```
                                                     SEQ ID NO: 13
QVQLVQSGAEVKKPGASVKVSCKASGYAFTNYWLGWVRQAPGHGLEWMGD

IYPGNGNSYYAQKFQGRVTMTRDKSSSTVYMELSSLRSEDTAVYFCTRSS

SYYRDVMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK

SEQ ID NO: 14
QVQLVQSGAEVKKPGASVKVSCKASGYAFTNYWLGWVRQAPGHGLEWMGD

IYPGNGNSYYAQKFQGRVTMTRDKSSSTVYMELSSLRSEDTAVYFCTRSS

SYYRDVMDYWGQGTLVTVSSASTKGPSVFPLAPCSRSTSESTAALGCLVK

DYFPEPVTVSWNSGALTSGVHTFPAVLQSSGLYSLSSVVTVPSSSLGTKT
```

```
YTCNVDHKPSNTKVDKRVESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK
```

The humanized light chain variable region sequence of the ab1 obtained in the embodiment 6 is spliced with the light chain constant region sequence of the human kappa to obtain a humanized ab1 light chain complete sequence. The sequence is shown in SEQ ID NO: 15.

```
                                                     SEQ ID NO: 15
DIQLTQSPSFLSASVGDRVTITCRASENIYSYLVWYQQKPGKAPKLLIYN

AKTLAEGVPSRFSGSGSGTEFTLTISSLQPEDFATYYCQHHYGTPLTFGA

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

Transient transfection of the CHO-K1 cells is carried out by the expression vector containing the complete sequence of the humanized ab1; and the humanized ab1 IgG1 antibody and the IgaG4 antibody required by an in vivo pharmacological experiment of a mouse tumor model are obtained through Protein A affinity chromatography and purification and ion-exchange chromatography and purification.

Figure 6:
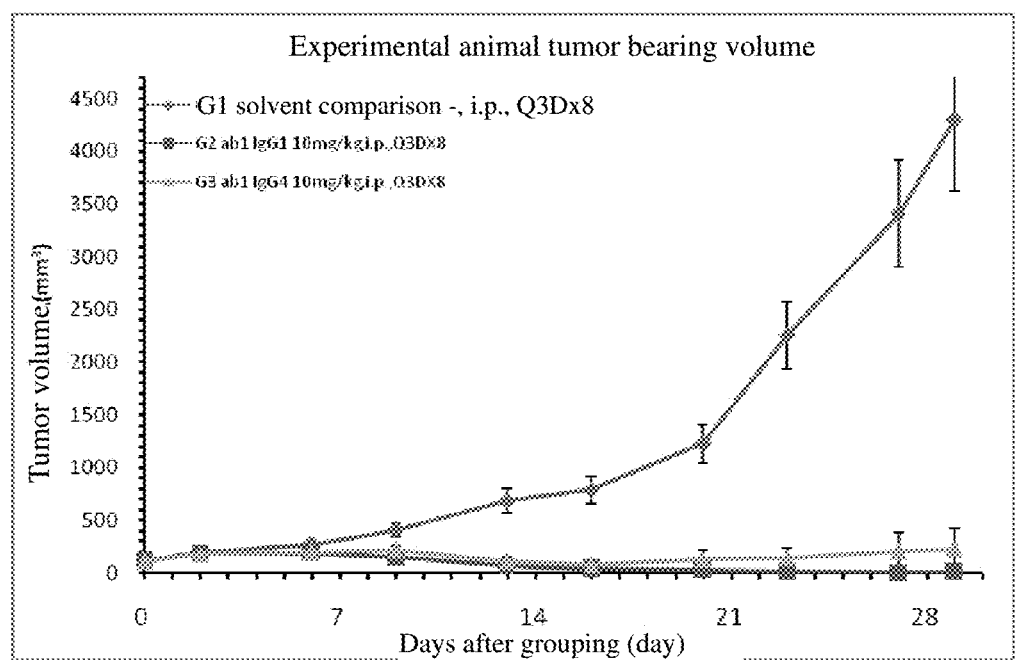
FIG. 6 is a graph showing the effect of ab1 humanized monoclonal antibody on tumor volume in a mouse MC38 tumor model.

5*10<5>/0.1 mL of MC38 colon cancer cells are inoculated subcutaneously into the right anterior rib of female B-h4-1BB humanized mice; the mice are grouped randomly according to the volume of the tumors after the tumors grow to about 150 mm$^3$; each group includes six mice; and two groups are in total, including, a control group (PBS solvent) and an experimental group (humanized ab1 IgG1 and humanized ab1 IgG4). The administration route is intraperitoneal injection at a dose of 10 mg/kg of the body weight, the administration frequency is 1 dos/3 days, the number of administrations is 8 in total, and the experiment is terminated after the 21st day of the grouped administration. Tumor volume and body weight are measured twice a week, and body weight and tumor volume of each mouse are recorded. At the end of the experiment, the animals are euthanized, the tumors are stripped, weighted and photographed, and the relative tumor inhibition rate (TGI) and tumor weight inhibition rate (IRTW) are calculated. The results of tumor volume changes of the anti-human 4-1BB monoclonal antibody against the mouse MC38 tumor model are shown in FIG. 6. From the results analysis, the relative tumor inhibition rates (TGI) of ab1 IgG1 and ab1 IgG4 are 99.84% and 94.61%, respectively, and the tumors of the animals to be administrated almost completely disappear.

What is claimed is:

1. An agonistic 4-1BB monoclonal antibody or an antigen binding fragment thereof, wherein the agonistic 4-1BB monoclonal antibody or the antigen-binding fragment thereof comprises a heavy chain variable region and a light chain variable region; the heavy chain variable region comprises a CDR1 region having the amino acid sequence as shown in SEQ ID NO: 1, a CDR2 region having the amino acid sequence as shown in SEQ ID NO: 2, and a CDR3 region having the amino acid sequence as shown in SEQ ID NO: 3; and the light chain variable region comprises a CDR1 region having the amino acid sequence as shown in SEQ ID NO: 4, a CDR2 region having the amino acid sequence as shown in SEQ ID NO: 5, and a CDR3 region having the amino acid sequence as shown in SEQ ID NO: 6.

2. The agonistic 4-1BB monoclonal antibody or the antigen binding fragment thereof according to claim 1, wherein the agonistic 4-1BB monoclonal antibody or the antigen binding fragment thereof comprises the heavy chain variable region as shown in SEQ ID NO: 7.

3. The agonistic 4-1BB monoclonal antibody or the antigen binding fragment thereof according to claim 1, wherein the agonistic 4-1BB monoclonal antibody or the antigen binding fragment thereof comprises the light chain variable region as shown in SEQ ID NO: 8.

4. The agonistic 4-1BB monoclonal antibody or the antigen binding fragment thereof according to claim 1, wherein the agonistic 4-1BB monoclonal antibody has one or more of the following properties:
  (a) activating T cells,
  (b) inhibiting tumor cell growth, and
  (c) treating cancers.

5. The agonistic 4-1BB monoclonal antibody or the antigen binding fragment thereof according to claim 1, wherein the agonistic 4-1BB monoclonal antibody comprises a heavy chain and a light chain.

6. The agonistic 4-1BB monoclonal antibody or the antigen binding fragment thereof according to claim 1, wherein the agonistic 4-1BB monoclonal antibody is IgG, IgA, IgE, IgM or IgD.

7. The agonistic 4-1BB monoclonal antibody or the antigen-binding fragment thereof according to claim 6, wherein the agonistic 4-1BB monoclonal antibody is IgG1, IgG2, IgG3 or IgG4.

8. The agonistic 4-1BB monoclonal antibody or the antigen-binding fragment thereof according to claim 6, wherein the agonistic 4-1BB monoclonal antibody is IgG1.

9. The agonistic 4-1BB monoclonal antibody or the antigen binding fragment thereof according to claim 1, wherein the agonistic 4-1BB antibody or antigen binding fragment thereof is humanized.

10. A pharmaceutical composition comprising the humanized antibody of claim 9 and a pharmaceutically acceptable carrier.

11. A pharmaceutical composition, comprising the agonistic 4-1BB monoclonal antibody or the antigen-binding fragment thereof of claim 1, and a pharmaceutically acceptable carrier.

12. A humanized anti-human 4-1BB antibody wherein the humanized anti-human 4-1BB antibody comprises a light chain and a heavy chain, the sequence of the light chain is as shown in SEQ ID NO:9 and the sequence of the heavy chain is as shown in SEQ ID NO:10.

13. A nucleic acid encoding the agonistic 4-1BB monoclonal antibody or the antigen-binding fragment thereof of claim 1.

14. A host cell comprising the nucleic acid of claim 13.

* * * * *